United States Patent [19]

Kiefer

[11] Patent Number: 5,714,604
[45] Date of Patent: Feb. 3, 1998

[54] PROCESS FOR THE PREPARATION OF AZAMACROCYCLIC OR ACYCLIC AMINOPHOSPHONATE ESTER DERIVATIVES

[75] Inventor: Garry E. Kiefer, Lake Jackson, Tex.

[73] Assignee: The Dow Chemical Company, Midland, Mich.

[21] Appl. No.: 65,963

[22] Filed: May 6, 1993

[51] Int. Cl.$^6$ .................... C07D 257/08; C07F 9/6524
[52] U.S. Cl. .................... 540/472; 540/474; 540/450; 540/471
[58] Field of Search .................... 540/472, 474, 540/450, 471; 558/115; 562/10, 14

[56] References Cited

U.S. PATENT DOCUMENTS

| | | | |
|---|---|---|---|
| 5,236,695 | 8/1993 | Winchell et al. | 424/9 |
| 5,342,936 | 8/1994 | Parker et al. | 540/474 |
| 5,385,893 | 1/1995 | Kiefer | 514/80 |
| 5,606,053 | 2/1997 | Prashad et al. | 540/474 |
| 5,630,997 | 5/1997 | Sherry et al. | 540/474 |

FOREIGN PATENT DOCUMENTS

| | | |
|---|---|---|
| 0382582 | 8/1990 | European Pat. Off. |
| 9001034 | 2/1990 | WIPO . |
| 90/09388 | 8/1990 | WIPO . |
| 9107911 | 6/1991 | WIPO . |

OTHER PUBLICATIONS

Maier, *Phosphorus and Sulfur*, (1987), vol. 33 (1–2), pp. 41–52.
Natcher, *Synthesis*, vol. 12, (1987), pp. 1079–1084.
Maier et al., Chemical Abstract 109(13): 110517a (1987) with STN Printout.
Chemical Abstracts Service Registry Handbook Number Section 1965–1971, No. 30525–89–4.

*Primary Examiner*—John M. Ford
*Assistant Examiner*—Pavanaram K. Sripada
*Attorney, Agent, or Firm*—Karen L. Kimble

[57] ABSTRACT

A novel process for the preparation of azamacrocyclic or acyclic aminophosphonate ester derivatives is disclosed. The process concerns the reaction of an appropriate azamacrocyclic or acyclic primary or secondary amine with trialkyl phosphite and paraformaldehyde.

10 Claims, No Drawings

PROCESS FOR THE PREPARATION OF AZAMACROCYCLIC OR ACYCLIC AMINOPHOSPHONATE ESTER DERIVATIVES

This invention concerns a novel process for the preparation of azamacrocyclic or acyclic aminophosphonate ester derivatives. Such process provides ligands which are useful as diagnostic or therapeutic agents.

BACKGROUND OF THE INVENTION

Macrocyclic aminophosphate esters are receiving considerable attention as diagnostic and therapeutic agents. The general synthetic methodology for preparing chelating agents of this type utilizes an amine in combination with phosphorous acid, formaldehyde and hydrochloric acid to provide the aminophosphonic acid, e.g. 1,4,7,10-tetraazacyclododecane-1,4,7,10-tetramethylenephosphonic acid (DOTMP). Alternatively, methylenephosphonate functionality can be introduced by substituting a di- or tri-alkyl phosphite in the place of phosphorous acid in the prior procedure, to generate the corresponding dialkylphosphonate ester. These esters can be hydrolyzed under basic conditions to give the monoalkylphosphonate half esters. In addition these full esters can be hydrolyzed under acidic conditions to give phosphonic acids, e.g. DOTMP (see published application WO 91/07911). The general synthetic approach to aminophosphonates using either di- or tri-alkyl phosphites is documented in the literature by the reaction of various linear amines and using standardized procedures.

SUMMARY OF THE INVENTION

The present invention is directed to a process for preparing azamacrocyclic or acyclic aminophosphonate ester derivatives which possess at least one secondary or primary nitrogen atom substituted with at least one moiety of the formula $$—CH_2PO_3RR^1 \qquad (I)$$

wherein

R is H or $C_1$–$C_5$ alkyl;

with the proviso that each R is the same group;

$R^1$ is $C_1$–$C_5$ alkyl, H, Na or K;

with the proviso that each R and $R^1$ is the same group when $C_1$–$C_5$ alkyl;

which comprises reacting the corresponding unsubstituted amine compound with a trialkyl phosphite and paraformaldehyde to provide the derivatives having at least two moieties of Formula (I) wherein all R and $R^1$ equal $C_1$–$C_5$ alkyl;

optionally followed by aqueous base hydrolysis to provide the derivatives having at least two moieties of Formula (I) wherein R is $C_1$–$C_5$ alkyl and $R^1$ is H, Na or K;

optionally followed by acid hydrolysis to provide the derivatives having at least two moieties of Formula (I) wherein all R and $R^1$ equal H.

When the above ligands having at least two moieties of Formula (I) have:

all R and $R^1$ equal H, the ligands are referred to as phosphonic acids;

all R equal H, and all $R^1$ equal $C_1$–$C_5$ alkyl, the ligands are referred to herein as phosphonate half esters;

all R and $R^1$ equal $C_1$–$C_5$ alkyl, the ligands are referred to as phosphonate esters.

In some of our copending applications and patents we have discussed the use of these azamacrocyclic or acyclic aminophosphonate ester derivatives having at least two moieties of Formula (I) as diagnostic agents. Particularly, the half esters are useful as tissue specific MRI contrast agents when chelated with gadolinium.

DETAILED DESCRIPTION OF THE INVENTION

The compounds having at least two moieties of Formula (I) which are azamacrocyclic or acyclic aminophosphonate ester derivatives which possess at least two secondary or primary nitrogen atoms each substituted with at least one moiety of the formula $$—CH_2PO_3RR^1 \qquad (I)$$

wherein

R is H or $C_1$–$C_5$ alkyl;

with the proviso that each R is the same group;

$R^1$ is $C_1$–$C_5$ alkyl, H, Na or K;

with the proviso that each R and $R^1$ is the same group when $C_1$–$C_5$ alkyl;

encompass known ligands and also those claimed in our copending applications.

The ligands used as starting materials to make the compounds having at least two moieties of Formula (I) are known in the art. Some examples of these acylic amine ligands are ethylenediamine (EDA);

diethylenetriamine (DTA);

triethylenetetraamine (TTA);

and numerous known linear or branch chain primary or secondary amines.

Some examples of azamacrocyclic amine ligands are 1,4,7,10-tetraazacyclododecane (Cyclen); and other known secondary azamacrocyclic amines.

Examples of suitable azamacrocyclic amine ligands that are discussed in our copending applications are shown by the following formula:

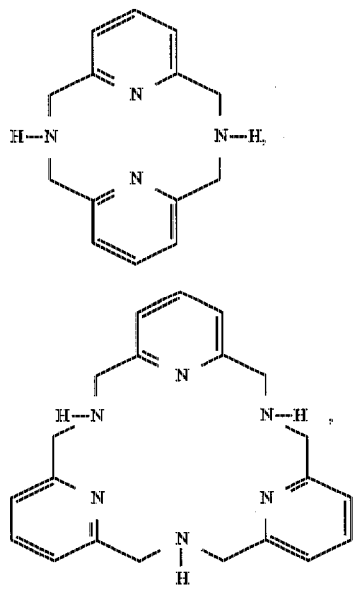

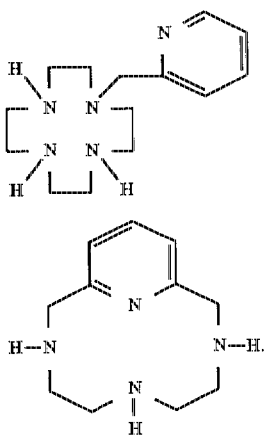

The terms used in Formula (I) and for this invention are further defined as follows. "$C_1$–$C_5$ alkyl", include both straight and branched chain alkyl groups. "Trialkyl phosphite" includes any alkyl which in the resulting product having at least two moieties of Formula (I) has desirable water solubility following hydrolysis, e.g. tri($C_1$–$C_{10}$ alkyl) phosphite, preferably tri($C_1$–$C_4$ alkyl)phosphite, including both straight and branched chain alkyl groups.

When the azamacrocyclic ligands having at least two moieties of Formula (I) wherein the full esters (R and $R^1$ are both the same $C_1$–$C_5$ alkyl) are prepared, pressure is not critical so that ambient pressure is used. As the reaction is exothermic, the temperature is controlled to be maintained below 40° C. during the first hour; and after the first hour, the temperature can be raised to facilitate completion of the reaction but need not exceed about 90° C. The pH of the reaction is not critical and the reaction is non-aqueous. The reaction is run in the presence of a non-aqueous liquid, such as the trialkyl phosphite reagent or a solvent. A solvent is preferably used, examples of such solvents are: aprotic polar solvents such as tetrahyrdofuran (THF), dioxane, acetonitrile, and other similar inert, non-aqueous solvents; alcohols where the alkyl portion is the same as the R obtained, such as methanol, ethanol and propanol. THF is the preferred solvent. The order of addition of the reactants and the azamacrocyclic or acyclic aminophosphonate starting material is not critical.

When the acyclic ligands having at least two moieties of Formula (I) wherein the full esters (R and $R^1$ are both the same $C_1$–$C_5$ alkyl) are prepared, the reaction is significantly more exothermic. It is critical to control the temperature below 40° C. for the first hour of the reaction. Methods to effectively control the temperature are known such as the presence of an ice bath, dilution with solvents or the order and/or speed of addition of reagents. For example, one method involves combining the trialkyl phosphite and paraformaldehyde and initially cooling the mixture, followed by the controlled addition of the acyclic amine, while maintaining the temperature by using an ice bath.

All the ligands having at least two moieties of Formula (I) wherein the half esters are prepared (R=$C_1$–$C_5$ alkyl and $R^1$=H, Na or K) by aqueous base hydrolysis is accomplished after the formation of the corresponding full ester. Examples of suitable bases are alkali metal hydroxides, e.g. sodium or potassium hydroxide. The amount of base used is from about 1–10 equivalents per secondary amine or 2–20 equivalents per primary amine. As the alkyl chain length of the R or $R^1$ group is propyl or higher, then a cosolvent is used with the water. Suitable examples of such cosolvents are organic water missible solvent, such as 1,4-dioxane, THF and acetone.

The full acids of the ligands having at least two moieties of Formula (I) may be made from the corresponding half esters or full esters under known acidic hydrolysis conditions (see published application WO 91/07911).

The present process is advantageous over those methods known in the art for the following reasons. The prior processes in which dialkyl phosphites under aqueous conditions are used give good results for acyclic amines but less predictable results are obtained when macrocyclic ligands are employed. Furthermore, the macrocyclic ligand pyclen is used, none of the desired ester is isolated. In contrast to the art, when the present process is used, the desired products having at least two moieties of Formula (I) are obtained in all instances with yields in excess of 90%.

The invention will be further clarified by a consideration of the following examples, which are intended to be purely exemplary of the present invention. Some terms used in the following examples are defined as follows: g=gram(s); mg=milligrams; kg=kilogram(s); mL=milliliter(s); µL=microliter(s).

General Materials and Methods.

All reagents were obtained from commercial suppliers and used as received without further purification. NMR spectra were recorded on a Bruker AC-250 MHz spectrometer equipped with a multi-nuclear quad probe ($^1$H, $^{13}$C, $^{31}$P, and $^{19}$F) at 297° K unless otherwise indicated. $^1$H spectra in $D_2O$ were recorded by employing solvent suppression pulse sequence ("PRESAT", homo-nuclear presaturation). $^1$H spectra are referenced to residual chloroform (in $CDCl_3$) at $\delta7.26$ or external dioxane (in $D_2O$) at $\delta3.55$. $^{13}$C and $^{31}$P spectra reported are proton decoupled (broad band). Assignments of $^{13}$C {$^1$H} chemical shifts were aided by DEPT (Distortionless Enhancement by Polarization Transfer) experiments. $^{13}$C {$^1$H} spectra are referenced to center peak of $CDCl_3$ at $\delta77.00$ (in $CDCl_3$) and external dioxane at $\delta66.66$ (in $D_2O$). $^{31}$P {$^1$H} spectra were referenced to external 85% $H_3PO_4$ at $\delta0.00$. Melting points were determined by capillary melt methods and were uncorrected. Semi-preparative ion-exchange chromatographic separations were performed at low pressure (<600 psi) using a standard glass column fitted with hand-packed Q-Sepharose™ (anion exchange) or SP-Sepharose™ (cation exchange) glass column, and with on-line UV detector at 263 nm for eluent monitoring. GC/MS spectra were performed on a Hewlett Packard 5890A Gas Chromatograph/5970 Mass Selective Detector.

The process to make the full ester derivatives having at least two moieties of Formula (I) has been discussed before. A typical procedure is as follows:

EXAMPLE 1

Process for preparing 1,4,7,10-tetraazacyclododecane-1,4,7,10-methylenedibutyl phosphonate Cyclen, 10 g (58 mmol), tributyl phosphite, 62 g (246 mmol) and paraformaldehyde, 7.4 g (246 mmol) were combined in 70 mL of THF and stirred at room temperature (the temperature was maintained below 40° C.) for 24 hrs. The homogeneous solution was then concentrated in vacuo to give a viscous oil (quantative yield) and characterized by:

$^1$H NMR ($CDCl_3$) δ 0.88 (m, 24H), 1.33 (m, 16H), 1.59 (m, 16H), 2.80 (s, 16H), 2.90 (d, 8H), 4.00 (m, 16H); and $^{13}$C {$^1$H} NMR ($CDCl_3$) δ 13.51, 18.65, 32.49, 32.57, 49.04, 51.45, 53.10, 53.18; and $^{31}$P NMR (CDCl$_3$) δ 26.16 (s, 4P); and is illustrated by the formula

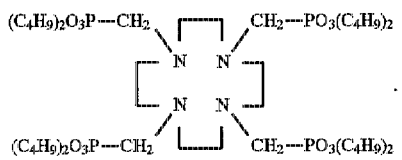

EXAMPLE 2

Process for preparing 1,4,7,10-tetraazacyclododecane-1,4,7,10-methylenediethyl phosphonate When the procedure of Example 1 was repeated using triethyl phosphite in place of the tributyl phosphite, the title compound was obtained as viscous oil in greater than 98% yield and characterized by:

$^{13}$C NMR (CDCl$_3$) δ 1.19 (m, 24H), 2.71 (s, 16H), 2.80 (d, 8H), 4.01 (m, 16H); and {$^1$H} NMR (CDCl$_3$) δ 15.32, 15.42, 42.23, 51.67, 53.18, 53.28, 61.34, 61.45; and $^{31}$P NMR (CDCl$_3$) δ 26.02 (s, 4P); and is illustrated by the formula

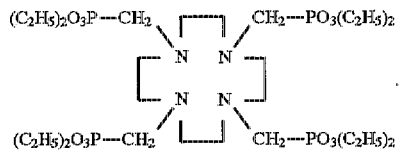

EXAMPLE 3

Preparation of N,N'-bis(methylenedimethylphosphonate)-2,11-diaza[3.3](2,6)pydinophane When the procedure of Example 1 was repeated using trimethyl phosphite in place of the tributyl phosphite and 2,11-diaza[3.3](2,6)pydinophane in place of Cyclen, the title compound was obtained as a very viscous oil in greater than 95% yield and further characterized by:

$^1$H NMR (CDCl$_3$) δ 3.39 (d, 4H), 3.88 (d, 12H), 4.08 (s, 8H), 6.84 (d, 4H), 7.13 (t, 2H); and $^{13}$C {$^1$H} (CDCl$_3$) δ 52.75 (d), 54.88 (d), 65.21 (d), 122.71, 135.69, 157.14; and $^{31}$P NMR (CDCl$_3$) δ 27.22; and is illustrated by the formula

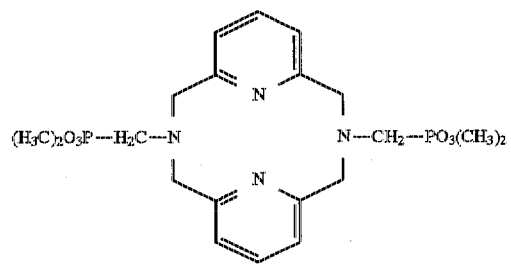

EXAMPLE 4

Preparation of N,N'-bis(methylenediethylphosphonate)-2,11-diaza[3.3](2,6)pydinophane When the procedure of Example 1 was repeated using triethyl phosphite in place of the tributyl phosphite and 2,11-diaza[3.3](2,6)pydinophane in place of Cyclen, the title compound was obtained as a very viscous oil in greater than 95% yield and further characterized by:

$^1$H NMR (CDCl$_3$) δ 1.24 (t, 12H), 3.20 (d, 4H), 3.94 (s, 8H), 4.07 (q, 8H), 6.71 (d, 4H), 6.98 (t, 2H); and $^{13}$C {$^1$H} NMR (CDCl$_3$) δ 16.48, 55.36 (d), 61.75 (d), 65.14 (d), 122.52, 135.41, 157.04; and $^{31}$P {$^1$H} NMR (CDCl$_3$) δ 24.60; and is illustrated by the formula

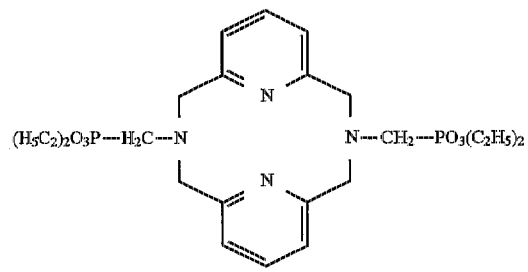

EXAMPLE 5

Preparation of N-(2-pyridylmethyl)-N',N'',N'''-tris(methylenediethylphosphonate)-1,4,7,10-tetraazacyclododecane When the procedure of Example 1 was repeated using triethyl phosphite in place of the tributyl phosphite and N-(2-pyridylmethyl)-1,4,7,10-tetraazacyclododecane in place of Cyclen, the title compound was obtained as a very viscous oil in greater than 95% yield and further characterized by:

$^1$H NMR (CDCl$_3$) δ 1.25–1.39 (m, 18H), 2.66–2.95 (m, 22H), 3.71 (s, 2H), 4.01–4.22 (m, 12H), 7.10–7.15 (m, 1H), 7.57–7.65 (m, 2H), 8.46–8.52 (m, 1H);

$^{13}$C {$^1$H} NMR (CDCl$_3$) δ 16.38, 16.46, 50.45, 50.67, 52.41, 53.19, 53.29, 53.48, 53.58, 61.37, 61.47, 61.52, 121.67, 123.28, 136.19, 148.61, 159.90; and $^{31}$P {$^1$H} NMR (CDCl$_3$, 297K) δ 26.21;

$^{31}$P {$^1$H} NMR (CDCl$_3$, 217K) δ 24.18 (1P), 24.32 (2P); and is illustrated by the formula

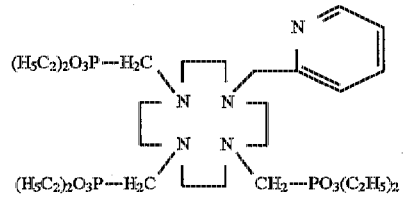

EXAMPLE 6

Preparation of N-(2-pyridylmethyl)-N',N'',N'''-tris(methylenedipropylphosphonate)-1,4,7,10-tetraazacyclododecane When the procedure of Example 1 was repeated using tripropyl phosphite in place of the tributyl phosphite and N-(2-pyridylmethyl)-1,4,7,10-tetraazacyclododecane in place of Cyclen, the title compound was obtained as a viscous oil in greater than 95% yield and further characterized by:

$^1$H NMR (CDCl$_3$) δ 0.91–1.00 (m, 18H), 1.60–1.76 (m, 12H), 2.67–2.99 (m, 22H), 3.73 (s, 2H), 3.94–4.08 (m, 12H), 7.12–7.15 (m, 1H), 7.46–7.67 (m, 2H), 8.48–8.52 (m, 1H);

$^{13}$C {$^1$H} NMR (CDCl$_3$) δ 9.93, 10.21, 23.71, 23.80, 50.17, 50.44, 52.38, 53.09, 53.44, 61.44, 66.79, 66.83, 121.61, 123.23, 136.14, 148.54, 159.92; and $^{31}$P {$^1$H} NMR (CDCl$_3$) δ 26.20 (1P), 26.23 (2P); and is illustrated by the formula

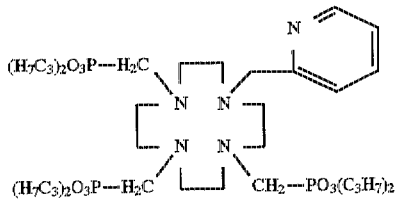

EXAMPLE 7

Preparation of 3,6,9,15-tetraazabicyclo[9.3.1] pentadeca-1(15),11,13-triene-3,6,9-methylenediethylphosphonate When the procedure of Example 1 was repeated using triethyl phosphite in place of the tributyl phosphite and 3,6,9,15-tetraazabicyclo[9.3.1]pentadeca-1(15),11,13-triene in place of Cyclen, the title compound was obtained as a viscous oil in greater than 95% yield and further characterized by:

$^1$H NMR (CDCl$_3$) δ 1.23 (m, 18H), 2.77 (m, 12H), 3.04 (d, 6H), 4.13 (m, 12H), 7.17 (d, 2H), 7.60 (t, 1H); and $^{13}$C NMR (CDCl$_3$) δ 16.43, 50.03, 50.31, 50.43, 50.77, 51.23, 51.38, 52.63, 53.30, 60.86, 60.92, 61.63, 61.74, 61.83, 61.93, 62.32, 76.46, 76.97, 77.18, 77.48, 122.50, 137.10, 157.18; and $^{31}$P NMR (CDCl$_3$) δ 24.92 (s, 2P), 24.97 (s, 1P); and is illustrated by the formula

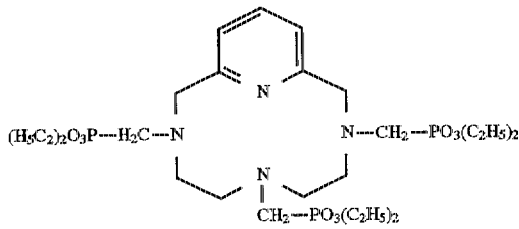

EXAMPLE 8

Preparation of 3,6,9,15-tetraazabicyclo[9.3.1] pentadeca-1(15),11,13-triene-3,6,9-methylenedi(n-propyl)phosphonate When the procedure of Example 1 was repeated using tripropyl phosphite in place of the tributyl phosphite and 3,6,9, 15-tetraazabicyclo[9.3.1]pentadeca-1(15),11,13-triene in place of Cyclen, the title compound was obtained as a viscous oil in greater than 95% yield and further characterized by:

$^1$H NMR (CDCl$_3$) δ 0.88 (m, 18H), 1.61 (m, 12H), 2.72 (m, 12H), 3.03 (d, 6H), 3.97 (m, 12H), 7.13 (d, 2H), 7.55 (t, 1H); and $^{13}$C NMR (CDCl$_3$) δ 9.96, 23.73, 49.84, 50.14, 50.26, 50.57, 51.11, 51.23, 52.43, 53.01, 60.78, 60.84, 67.27, 67.40, 122.48, 137.04, 157.16; and $^{31}$P NMR (CDCl$_3$) δ 24.98 (3P); and is illustrated by the formula

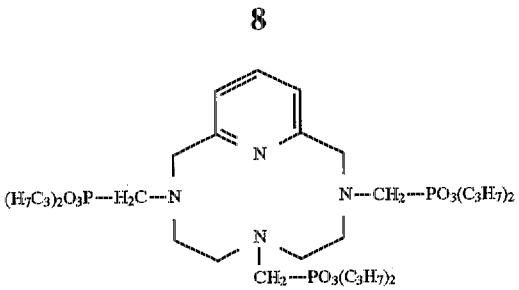

EXAMPLE 9

Preparation of 3,6,9,15-tetraazabicyclo[9.3.1] pentadeca-1(15),11,13-triene-3,6,9-methylenedi(n-butyl)phosphonate When the procedure of Example 1 was repeated using tributyl phosphite in place of the tributyl phosphite and 3,6,9,15-tetraazabicyclo[9.3.1]pentadeca-1(15),11,13-triene in place of Cyclen, the title compound was obtained as a viscous oil in greater than 95% yield and further characterized by:

$^1$H NMR (CDCl$_3$) δ 0.84 (m, 18H), 1.27 (m, 12H), 1.58 (m, 12H), 2.57 (m, 12H), 3.01 (d, 6H), 3.99 (m, 12H), 7.12 (d, 2H), 7.54 (t, 1H); and $^{13}$C NMR (CDCl$_3$) δ 13.42, 13.46, 18.50, 18.59, 32.16, 32.43, 49.88, 50.03, 50.16, 50.63, 51.11, 51.27, 52.48, 53.16, 60.71, 60.78, 65.38, 65.48, 65.58, 122.46, 136.96, 157.14; and $^{31}$P NMR (CDCl$_3$) δ 24.88 (2P), 24.93 (1P); and is illustrated by the formula

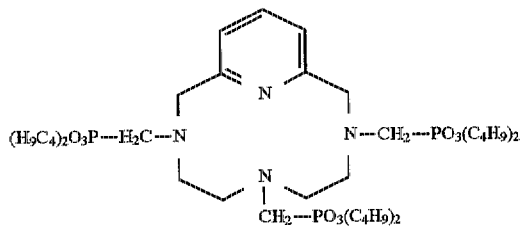

The process to hydrolyze with base the full ester derivatives having at least two moieties of Formula (I) to prepare the half esters having at least two moieties of Formula (I) has been discussed before. A typical procedure is as follows:

EXAMPLE 10

Preparation of 1,4,7,10-tetracyclododecane-1,4,7,10-tetramethylenebutylphosphonate, potassium salt The ester prepared in Example 1, 3 g (3 mmol) was combined in an aqueous dioxane solution (100 mL water:25 mL dioxane), along with 3 g of KOH (48 mmol). The solution was stirred at reflux for 16 hrs. The one desired titled product was obtained as a solid (94% yield) as characterized by:

$^{31}$P NMR (D$_2$O) δ 21.87 (s, 4P); and is illustrated by the formula

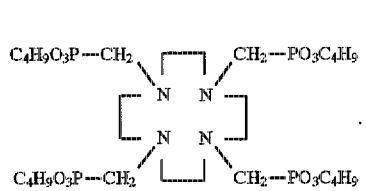

For other ester derivatives where the alkyl ester is $C_1$–$C_3$ alkyl, hydrolysis proceeds without the dioxane cosolvent.

EXAMPLE 11

Preparation of N,N'-bis(methylenephosphonic acid ethyl ester)-2,11-diaza[3.3](2,6)pydinophane (BP2EP)

When the procedure of Example 10 was repeated using ester of Example 4, the title compound was obtained as a solid in greater than 95% yield and further characterized by:

$^1$H NMR ($D_2O$) δ 1.10 (t, 6H), 2.97 (d, 4H), 3.81 (q, 4H), 3.84 (s, 8H), 6.73 (d, 4H), 7.09 (t, 2H); and $^{13}$C {$^1$H} NMR ($D_2O$) δ 18.98, 58.76 (d), 63.69 (d), 66.53 (d), 126.35, 140.09, 159.37; and $^{31}$P {$^1$H} NMR ($D_2O$) δ 20.65; and is illustrated by the formula

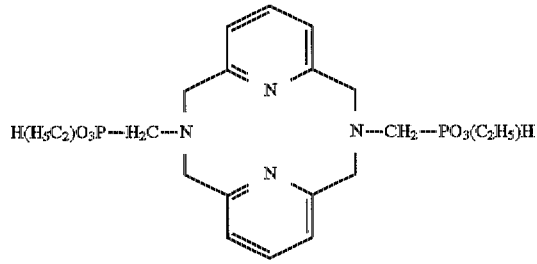

EXAMPLE 12

Preparation of 3,6,9,15-tetraazabicyclo[9.3.1] pentadeca-1(15),11,13-triene-3,6,9-methylene(n-butyl)phosphonate tris(potassium salt) (PMBHE)

When the procedure of Example 10 was repeated using ester of Example 9, the title compound was obtained as a solid in greater than 95% yield and further characterized by:

$^1$H NMR ($D_2O$) δ 0.68 (m, 9H), 1.14 (m, 6H), 1.37 (m, 6H), 2.76 (d, 6H), 3.41 (m, 12H), 3.73 (m, 6H), 7.24 (d, 2H), 7.76 (t, 1H); and $^{13}$C NMR ($D_2O$) δ 15.76, 15.80, 21.12, 21.20, 34.96, 35.06, 35.14, 52.08, 52.53, 53.38, 53.48, 54.49, 54.75, 57.70, 57.76, 61.86, 67.65, 67.75, 67.98, 68.08, 125.15, 142.93, 152.25; and $^{31}$P NMR δ 9.73 (s, 2P), 21.00 (s, 1P); and is illustrated by the formula

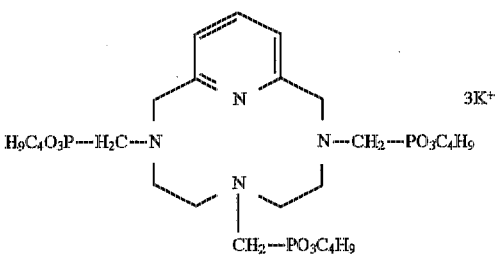

EXAMPLE 13

Preparation of 3,6,9,15-tetraazabicyclo[9.3.1] pentadeca-1(15),11,13-triene-3,6,9-methylene(n-propyl)phosphonate tris(potassium salt) (PMPHE)

When the procedure of Example 10 was repeated using ester of Example 8, the title compound was obtained as a solid in greater than 95% yield and further characterized by:

$^{31}$P NMR δ 20.49 (s, 3P); and is illustrated by the formula

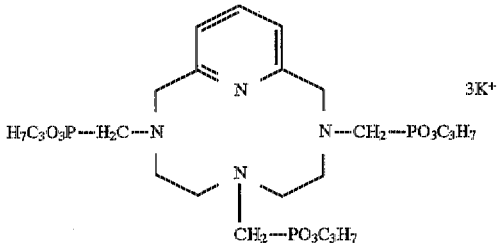

EXAMPLE 14

Preparation of 3,6,9,15-tetraazabicyclo[9.3.1] pentadeca-1(15),11,13-triene-3,6,9-methyleneethylphosphonate tris(potassium salt) (PMEHE)

When the procedure of Example 10 was repeated using ester of Example 7, the title compound was obtained as a solid in greater than 95% yield and further characterized by:

$^{13}$C NMR ($D_2O$) δ 18.98, 19.82, 51.78, 52.06, 53.08, 54.46, 54.68, 57.01, 58.22, 60.24, 63.19, 63.25, 63.36, 63.49, 63.59, 63.95, 64.18, 64.25, 66.80, 126.62, 141.63, 159.40; and $^{31}$P NMR ($D_2O$) δ 20.58 (s, 2P), 20.78 (s, 1P); and is illustrated by the formula

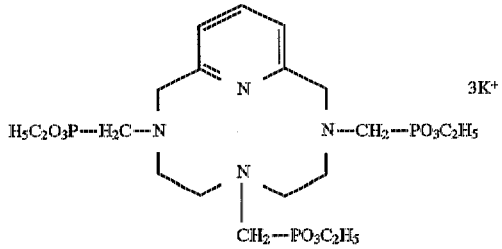

EXAMPLE 15

Preparation of N-(2-pyridylmethyl)-N',N'',N'''-tris (methylenephosphonic acid ethyl ester)-1,4,7,10-tetraazacyclododecane (PD3EP)

When the procedure of Example 10 was repeated using ester of Example 5, the title compound was obtained as a solid in greater than 95% yield and further characterized by:

$^1$H NMR (D$_2$O, 338 K) δ 1.41–1.57 (m, 9H), 3.28–3.89 (m, 22H), 4.09–4.64 (m, 8H), 8.22–8.26 (m, 2H), 8.70–8.75 (m, 1H), 9.00–9.12 (m, 1H); and $^{13}$C {$^1$H} NMR (D$_2$O, 338 K) δ 19.41, 19.51, 52.58, 53.00, 52.31, 53.75, 53.82, 56.04, 59.53, 64.60, 64.76, 129.86, 131.41, 147.31, 149.06, 154.34; and $^{31}$P {$^1$H} NMR (D$_2$O, 338K) δ 9.64 (2P), 19.79 (1P); and is illustrated by the formula

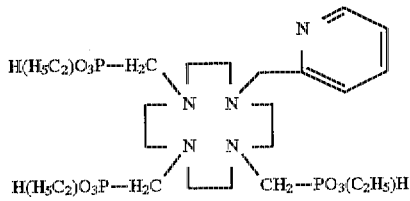

EXAMPLE 16

Preparation of N-(2-pyridylmethyl)-N',N'',N'''-tris (methylenephosphonic acid propyl ester)-1,4,7,10-tetraazacyclododecane (PD3PP)

When the procedure of Example 10 was repeated using ester of Example 6, the title compound was obtained as a solid in greater than 95% yield and further characterized by:

$^1$H NMR (D$_2$O, 353 K) δ 1.24–1.36 (m, 9H), 1.95–2.04 (m, 6H), 3.03–3.29 (m, 22H), 4.10–4.25 (m, 8H), 7.74–7.92 (m, 2H), 8.23–8.29 (m, 1H), 8.87–8.96 (m, 1H); and $^{13}$C {$^1$H} NMR (D$_2$O, 353 K) δ 13.15, 27.20, 50.43, 53.89, 54.48, 54.98, 55.42, 64.33, 69.41, 126.38, 128.30, 141.24, 152.46, 161.45; and $^{31}$P {$^1$H} NMR (D$_2$O, 353K) δ 21.61 (2P), 21.95 (1P); and is illustrated by the formula

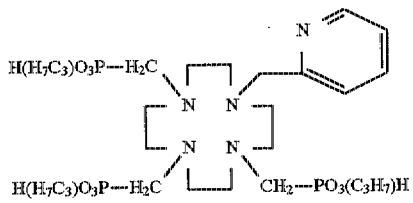

The process to make the phosphonic acid derivatives of Formula (I) has been discussed before. A typical procedure is as follows:

EXAMPLE 17

Preparation of Preparation of N,N'-bis (methylenephosphonic acid)-2,11-diaza[3.3](2,6) pydinophane (BP2P)

A conc. HCl solution (37%, 4 mL) of N,N'-bis (methylenedimethylphosphonate)-2,11-diaza[3.3](2,6) pydinophane, prepared in Example 3, (255 mg, 0.53 mmol) was heated at reflux for 2.5 hr. After cooling, the solution was evaporated to dryness, followed by coevaporation with fresh deionized water (3×2 mL) to eliminate excess HCl. The final product was isolated as a hygroscopic brown solid upon freeze-drying of the concentrated aqueous solution; and characterized by:

$^1$H NMR (D$_2$O) δ 3.55 (d, 4H), 4.46 (br s, 8H), 6.90 (d, 4H), 7.37 (t, 2H); and $^{13}$C {$^1$H} NMR (D$_2$O) δ 57.80 (d), 63.74 (d), 127.02, 144.18, 152.96; and $^{31}$P {$^1$H} NMR (D$_2$O) δ 11.71; and is illustrated by the formula

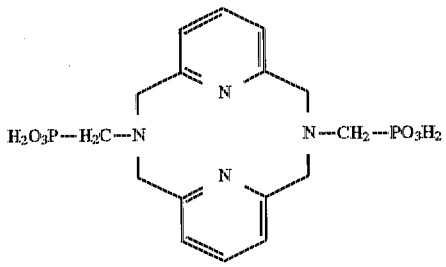

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A process for preparing azamacrocyclic aminophosphonate ester derivatives which possess at least two secondary or primary nitrogen atoms each substituted with at least one moiety of the formula $$-CH_2PO_3RR^1 \qquad (I)$$

wherein

R is H or C$_1$–C$_5$ alkyl;

with the proviso that each R is the same group;

R$^1$ is C$_1$–C$_5$ alkyl, H, Na or K;

with the proviso that each R and R$^1$ is the same alkyl group when both are C$_1$–C$_5$ alkyl;

which comprises reacting the corresponding unsubstituted amine compound with a trialkyl phosphite and paraformaldehyde, in a non-aqueous liquid, maintaining the temperature below 40° C. during at least the first hour of the reaction, to provide the aminophosphonate ester derivatives having at least two moieties of Formula (I) wherein all R and R$^1$ equal C$_1$–C$_5$ alkyl;

optionally followed by aqueous base hydrolysis to provide the aminophosphonate ester derivatives having at least two moieties of Formula (I) wherein R is C$_1$–C$_5$ alkyl and R$^1$ is H, Na or K;

optionally followed by acid hydrolysis to provide the aminophosphonate ester derivatives having at least two moieties of Formula (I) wherein all R and R$^1$ equal H.

2. The process of claim 1 wherein the aminophosphonate ester derivative, having at least two moieties of Formula (I), has all R and R$^1$ equal H.

3. The process of claim 1 wherein the aminophosphonate ester derivative, having at least two moieties of Formula (I), has all R equal H, and all R$^1$ equal C$_1$–C$_5$ alkyl.

4. The process of claim 1 wherein the aminophosphonate ester derivative, having at least two moieties of Formula (I), has all R and R$^1$ equal C$_1$–C$_5$ alkyl.

5. The process of claim 1 wherein the trialkyl phosphite is a tri(C$_1$–C$_4$ alkyl) phosphite.

6. The process of claim 1 wherein the aminophosphonate ester derivative, having at least two moieties of Formula (I), is an azamacrocyclic ligand where R and R$^1$ are both the same C$_1$–C$_5$ alkyl.

7. The process of claim 1 wherein the aminophosphonate ester derivative, having at least two moieties of Formula (I), is an azamacrocyclic ligand where R and R$^1$ are both the same C$_1$–C$_5$ alkyl, and a solvent is present.

8. The process of claim 7 wherein the solvent is tetrahydrofuran.

9. A process for preparing acyclic aminophosphonate ester derivatives which possess at least two secondary or primary nitrogen atoms each substituted with at least one moiety of the formula $$—CH_2PO_3RR^1 \qquad (I)$$

wherein

R is H or $C_1$–$C_5$ alkyl;

with the proviso that each R is the same group;

$R^1$ is $C_1$–$C_5$ alkyl, H, Na or K;

with the proviso that each R and $R^1$ is the same alkyl group when both are $C_1$–$C_5$ alkyl;

which comprises reacting the corresponding unsubstituted amine compound with a trialkyl phosphite and paraformaldehyde, maintaining the temperature below 40° C. during the first hour of the reaction, to provide the aminophosphonate ester derivatives having at least two moieties of Formula (I) wherein all R and $R^1$ equal $C_1$–$C_5$ alkyl;

optionally followed by aqueous base hydrolysis to provide the aminophosphonate ester derivatives having at least two moieties of Formula (I) wherein R is $C_1$–$C_5$ alkyl and $R^1$ is H, Na or K;

optionally followed by acid hydrolysis to provide the aminophosphonate ester derivatives having at least two moieties of Formula (I) wherein all R and $R^1$ equal H.

10. The process of claim 9 wherein the trialkyl phosphite and paraformaldehyde are combined and initially cooled, followed by the controlled addition of the acyclic amine, and the temperature is maintained by using an ice bath.

* * * * *